US010344125B2

(12) United States Patent
Le et al.

(10) Patent No.: US 10,344,125 B2
(45) Date of Patent: Jul. 9, 2019

(54) PURIFICATION OF 1,4-BIS (4-PHENOXYBENZOYL)BENZENE BY CENTRIFUGAL FILTRATION

(71) Applicant: ARKEMA FRANCE, Colombes (FR)

(72) Inventors: Guillaume Le, Hérouville-Saint-Clair (FR); Julien Jouanneau, Corneville-sur-Risle (FR); Jérôme Amstutz, Charly (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/982,549

(22) Filed: May 17, 2018

(65) Prior Publication Data
US 2018/0334538 A1 Nov. 22, 2018

(30) Foreign Application Priority Data
May 18, 2017 (EP) .................................... 17305583

(51) Int. Cl.
| C07C 41/00 | (2006.01) |
| C08G 65/00 | (2006.01) |
| C08G 65/40 | (2006.01) |
| C07C 49/84 | (2006.01) |
| C07C 41/36 | (2006.01) |
| C07C 7/148 | (2006.01) |
| C07C 45/46 | (2006.01) |
| C07C 45/80 | (2006.01) |
| C07C 45/79 | (2006.01) |

(52) U.S. Cl.
CPC ...... *C08G 65/4018* (2013.01); *C07C 7/14891* (2013.01); *C07C 41/36* (2013.01); *C07C 45/46* (2013.01); *C07C 45/79* (2013.01); *C07C 45/80* (2013.01); *C07C 49/84* (2013.01); *C08G 2650/40* (2013.01)

(58) Field of Classification Search
CPC ............................ C07C 41/36; C08G 2650/40
See application file for complete search history.

(56) References Cited

U.S. PATENT DOCUMENTS

| 4,716,211 | A | 12/1987 | Clendinning et al. |
| 4,816,556 | A | 3/1989 | Gay et al. |
| 4,826,947 | A | 5/1989 | Jansons et al. |
| 4,827,041 | A | 5/1989 | Ford et al. |
| 4,918,237 | A | 4/1990 | Corbin et al. |
| 4,931,530 | A | 6/1990 | Fukawa et al. |
| 5,734,005 | A | 3/1998 | Daniels et al. |

FOREIGN PATENT DOCUMENTS

| EP | 0 192 260 A1 | 8/1986 |
| EP | 0 268 112 A2 | 5/1988 |
| EP | 0 298 771 A2 | 1/1989 |
| EP | 0 316 133 A2 | 5/1989 |
| EP | 0 268 112 A3 | 11/1989 |
| GB | 2 287 031 A | 9/1995 |
| IN | 193687 | 7/2004 |
| SU | 445 643 A | 12/1975 |
| WO | WO 95/23821 A1 | 9/1995 |

OTHER PUBLICATIONS

U.S. Appl. No. 15/981,284, Jouanneau et al.
U.S. Appl. No. 15/981,439, Jouanneau et al.
U.S. Appl. No. 15/981,498, Jouanneau et al.
U.S. Appl. No. 15/982,625, Le et al.
U.S. Appl. No. 15/982,453, Jouanneau et al.
Database WPI Week 197630, AN 1976-57263X, Dec. 19, 1975, vol. 1976, No. 30,31, 1 page, Thomson Scientific, London, GB (XP002775200).
Banihashemi, Ahmad, et al., "New heat stable polyethers, polyketones and polysulfones", *Macromolecular Chemistry and Physics*, vol. 200, No. 10, Oct. 1, 1999, pp. 2284-2293, WILEY-VCH Verlag GmbH, Weinheim, DE (XP055420800).
Baysec, Sebnem, et al., "Very High Solid State Photoluminescence Quantum Yields of Poly(tetraphenylethylene) Derivatives", *Macromolecular Rapid Communications*, vol. 37, No. 22, Sep. 26, 2016, pp. 1802-1806, WILEY-VCH Verlag GmbH & Co. KGaA, Weinheim, DE (XP055420789).
Fukawa, Isaburo, et al., "Preparation of Dibenzofuran-Type Amorphous Polyetherketone by Novel Etherification Reaction", *Journal of Polymer Science: Part A: Polymer Chemistry*, 1992, pp. 1977-1985, vol. 30 (XP055420842).
March, Jerry, "Advanced Organic Chemistry", Dec. 31, 1985, p. 333, copyright page, John Wiley & Sons, New York (XP002775202).
Mithyantha, et al. , "A process for the purification of 1,4-bis(4-phenoxybenzoyl)benzene", Database Caplus [Online], Aug. 23, 2006, 1 page, Chemical Abstracts Service, Columbus, OH (XP002775201).
Streitwieser, Andrew, et al. , "Introduction to Organic Chemistry", Dec. 31, 1981, p. 544, copyright page, Macmillan Publishing Co., Inc., New York (XP002775203).
European Search Report in application No. EP 17305559.1, dated Nov. 9, 2017, European Patent Office, Munich, DE, 10 pages.
European Search Report in application No. EP 17305561.7, dated Nov. 3, 2017, European Patent Office, Munich, DE, 5 pages.
European Search Report in application No. EP 17305562.5, dated Dec. 6, 2017, European Patent Office, Munich, DE, 10 pages.
European Search Report in application No. EP 17305581.5, dated Nov. 24, 2017, European Patent Office, Munich, DE, 6 pages.
European Search Report in application No. EP 17305582.3, dated Nov. 8, 2017, European Patent Office, Munich, DE, 7 pages.
European Search Report in application No. EP 17305583.1, dated Aug. 22, 2017, European Patent Office, Munich, DE, 8 pages.

(Continued)

*Primary Examiner* — Sikarl A Witherspoon
(74) *Attorney, Agent, or Firm* — Buchanan Ingersoll & Rooney P.C.

(57) ABSTRACT

A method for manufacturing 1,4-bis(4-phenoxybenzoylbenzene), including: reacting terephthaloyl chloride with diphenyl ether in a reaction solvent and in the presence of a Lewis acid, so as to obtain a product mixture including a 1,4-bis (4-phenoxybenzoylbenzene)-Lewis acid complex; contacting the product mixture with a protic solvent, so as to obtain a first phase containing the Lewis acid and a second phase containing 1,4-bis(4-phenoxybenzoylbenzene); subjecting at least the second phase to a solid/liquid separation step by centrifugal filtration, so as to recover solid 1,4-bis(4-phenoxybenzoylbenzene).

15 Claims, 1 Drawing Sheet

(56) References Cited

OTHER PUBLICATIONS

Jouanneau, Julien M., et al., U.S. Appl. No. 15/981,284 entitled "Method for Manufacturing 1,4-Bis(4-Phenoxybenzoyl) Benzene at an Elevated Temperature," filed May 16, 2018.
Jouanneau, Julien M., et al., U.S. Appl. No. 15/981,439 entitled "Method for Manufacturing 1,4-Bis(4-Phenoxybenzoyl) Benzene in Supersaturation Conditions," filed May 16, 2018.
Jouanneau, Julien, et al., U.S. Appl. No. 15/981,498 entitled "Method for Manufacturing 1,4-Bis(4-Phenoxybenzoyl) Benzene Using Substantially Non-Hydrolyzed Terephthaloyl Chloride," filed May 16, 2018.
Le, Guillaume, et al., U.S. Appl. No. 15/982,625 entitled "Dissociation of a 1,4-Bis(4-Phenoxybenzoyl)Benzene-Lewis Acid Complex in an Aqueous Solution," filed May 17, 2018.
Jouanneau, Julien, et al., U.S. Appl. No. 15/982,453 entitled "Ripening of 1,4-Bis(4-Phenoxybenzoyl)Benzene," filed May 17, 2018.

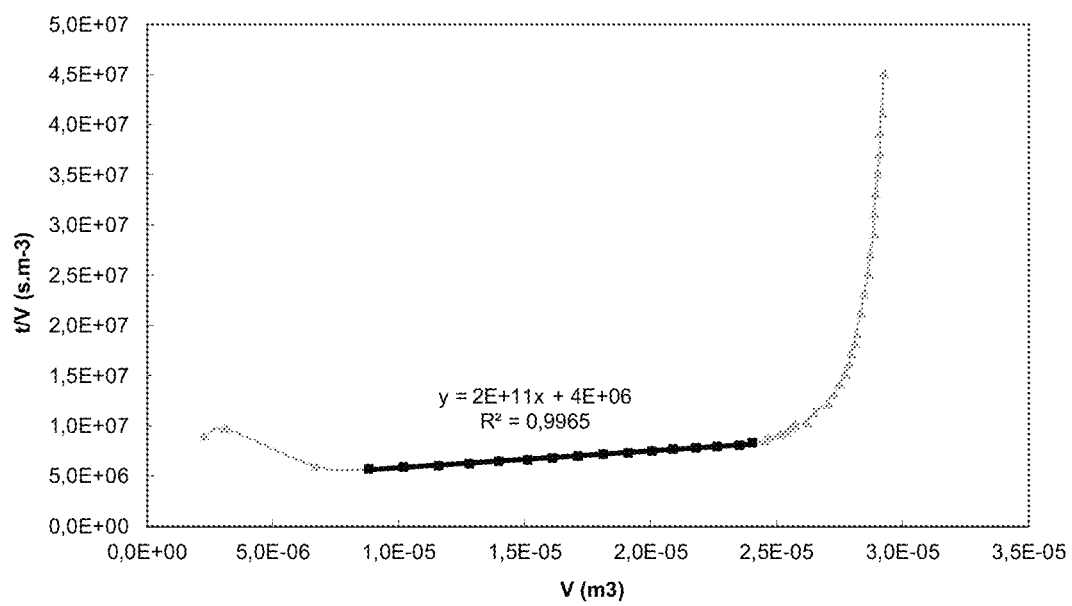

US 10,344,125 B2

PURIFICATION OF 1,4-BIS (4-PHENOXYBENZOYL)BENZENE BY CENTRIFUGAL FILTRATION

CROSS REFERENCE TO RELATED APPLICATIONS

The present application claims the benefit of European Application No. 17305583, filed on May 18, 2017. The entire contents of European Application No. 17305559, European Application No. 17305561, European Application No. 17305562, European Application No. 17305581, European Application No. 17305582, and European Application No. 17305583 are hereby incorporated herein by reference in their entirety.

TECHNICAL FIELD

The present application relates to a method for manufacturing 1,4-bis(4-phenoxybenzoylbenzene), as well as a method for manufacturing polyether ketone ketone polymers starting from said 1,4-bis(4-phenoxybenzoylbenzene).

TECHNICAL BACKGROUND

Polyether ketone ketone (PEKK) polymers have a number of properties which make them useful for applications involving exposure to high temperature or to high mechanical or chemical stress. They are for instance useful in the aerospace industry, in off-shore drilling and in medical devices.

One known route for manufacturing polyether ketone ketone polymers relies on the use of 1,4-bis(4-phenoxybenzoylbenzene) as a starting material.

1,4-bis(4-phenoxybenzoylbenzene) can be prepared by reacting terephthaloyl chloride and diphenyl ether in the presence of a Lewis acid such as aluminum trichloride.

In document U.S. Pat. No. 4,816,556 (example 2), 1,4-bis(4-phenoxybenzoylbenzene) is prepared by dissolving terephthaloyl chloride and diphenyl ether in ortho-dichlorobenzene and adding aluminum chloride. Thereafter, cold methanol is added so as to produce a slurry which is filtered, reslurried in methanol and filtered again.

In document U.S. Pat. No. 4,826,947 (example 2), 1,4-bis(4-phenoxybenzoylbenzene) is prepared by providing a mixture of methylene chloride, methylsulfone and aluminum trichloride, adding diphenyl ether and thereafter terephthaloyl chloride. The reaction mixture is then poured into cold methanol so as to make a slurry which is then filtered.

Document WO 95/23821 (example 11) discloses providing aluminum chloride in ortho-dichlorobenzene and then adding terephthaloyl chloride and diphenyl ether. Thereafter, the reaction mixture is allowed to warm up to room temperature, stirred, and poured into a methanol concentrated HCl solution. A precipitate is formed which is subsequently filtered off.

There is still a need for a method for manufacturing 1,4-bis(4-phenoxybenzoylbenzene) with a high purity and a high yield, which can be implemented at the industrial scale in an economically realistic manner.

SUMMARY

It is a first object of embodiments of the invention to provide a method for manufacturing 1,4-bis(4-phenoxybenzoylbenzene), comprising:

reacting terephthaloyl chloride with diphenyl ether in a reaction solvent and in the presence of a Lewis acid, so as to obtain a product mixture comprising a 1,4-bis(4-phenoxybenzoylbenzene)-Lewis acid complex;

contacting the product mixture with a protic solvent, so as to obtain a first phase containing the Lewis acid and a second phase containing 1,4-bis(4-phenoxybenzoylbenzene);

subjecting at least the second phase to a solid/liquid separation step by centrifugal filtration, so as to recover solid 1,4-bis(4-phenoxybenzoylbenzene).

In some embodiments, the first phase may contain at least 50% of the Lewis acid in the product mixture, more than 50% of the Lewis acid, at least 70% of the Lewis acid, at least 90% of the Lewis acid.

In some embodiments, the second phase may contain at least at least 50% of the 1,4-bis(4-phenoxybenzoylbenzene) in the product mixture, more than 50% of the 1,4-bis(4-phenoxybenzoylbenzene), at least 70% of the 1,4-bis(4-phenoxybenzoylbenzene), at least 90% of the 1,4-bis(4-phenoxybenzoylbenzene).

In some embodiments, the method comprises one or more steps of washing the recovered solid 1,4-bis(4-phenoxybenzoylbenzene) in a protic solvent, preferably methanol, and subjecting it to a further solid/liquid separation, preferably by centrifugal filtration.

In some embodiments, at least one of the steps of washing the solid 1,4-bis(4-phenoxybenzoylbenzene) is performed at a temperature of at least 20° C., preferably at a temperature of from 30 to 60° C.

In some embodiments, each step of washing the recovered the solid 1,4-bis(4-phenoxybenzoylbenzene) is performed in a centrifugal filtration device.

In some embodiments, the method further comprises:
separating the first phase from the second phase, preferably before subjecting the second phase to the solid/liquid separation step; and/or
heating the second phase up to a maximum temperature, followed by cooling the second phase down to a separation temperature, before subjecting the second phase to the solid/liquid separation step, and preferably after separating the first phase from the second phase.

In some embodiments, from 30 to 99.9 wt. %, preferably from 50 to 95 wt. %, more preferably from 60 to 90 wt. % of the 1,4-bis(4-phenoxybenzoylbenzene) contained in the second phase is dissolved in the second phase at the maximum temperature.

In some embodiments, the maximum temperature is from 90 to 150° C., preferably from 100 to 140° C., more preferably from 110 to 135° C.

In some embodiments, the separation temperature is at least 20° C., preferably is from 25 to 40° C.

In some embodiments, the second phase is cooled down at a rate of from 10 to 50° C./h, preferably from 20 to 40° C./h.

In some embodiments, the protic solvent that the product mixture is contacted with is an aqueous solution, which preferably has a pH of not more than 5, more preferably not more than 3 and most preferably not more than 2.

In some embodiments, the product mixture is poured into a vessel containing the protic solvent.

In some embodiments, the second phase is subjected to the solid/liquid separation step at a temperature of at least 20° C., preferably from 25 to 40° C.

In some embodiments, the Lewis acid is aluminum trichloride.

In some embodiments, the reaction solvent is a separate reaction solvent and may be ortho-dichlorobenzene. In some embodiments, the reaction solvent may be diphenyl ether.

It is another object of embodiments of the invention to provide a method of making a polyether ketone ketone polymer, comprising:

manufacturing 1,4-bis(4-phenoxybenzoylbenzene) according to the method described above;

reacting said 1,4-bis(4-phenoxybenzoylbenzene) with at least one difunctional aromatic acyl chloride.

Embodiments of the present invention provide a method for manufacturing 1,4-bis(4-phenoxybenzoylbenzene) with a high purity and a high yield. This method can be implemented at the industrial scale.

Reacting terephthaloyl chloride with diphenyl ether in the presence of a Lewis acid leads to the formation of a 1,4-bis(4-phenoxybenzoylbenzene)-Lewis acid complex. Then, this complex is dissociated by contacting it with a protic solvent, so as to recover free 1,4-bis(4-phenoxybenzoylbenzene) mostly in a solid (precipitated form). Said 1,4-bis(4-phenoxybenzoylbenzene) is then separated from the product mixture by a solid/liquid separation step.

According to embodiments of the present invention, the solid/liquid separation step may be performed by centrifugal filtration, in a centrifugal filtration device. It has been found that centrifugal filtration is particularly efficient and quick for performing the desired solid/liquid separation.

It may be especially advantageous to also wash the solid 1,4-bis(4-phenoxybenzoylbenzene) in situ in the centrifugal filtration device, without resuspending the solid in the solvent used for washing. It has surprisingly been found that despite limited contact time between the solid to be purified and the solvent in a centrifuge compared to conventional filtration, effective washing can be performed in this manner.

BRIEF DESCRIPTION OF THE DRAWINGS

FIG. 1 shows a graph of the filtration time divided by the filtered volume (t/V) as a function of the filtered volume (V) as obtained in example 3. The slope measured in this graph in the substantially linear area may be used in the Kozeny-Carman equation to calculate the specific cake resistance.

DESCRIPTION OF EMBODIMENTS

Embodiments of the invention will now be described in more detail without limitation in the following description.

1,4-bis(4-phenoxybenzoylbenzene) is the compound of formula I:

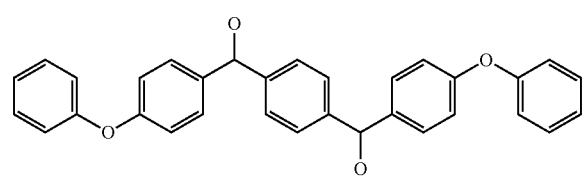
(I)

It may be made by reacting terephthaloyl chloride of formula II:

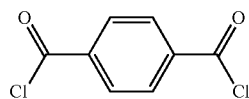
(II)

with diphenyl ether of formula III:

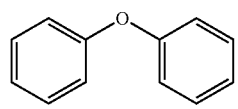
(III)

in a solvent (the reaction solvent), and in the presence of a Lewis acid, acting as a Friedel-Crafts catalyst.

The reaction results in the production of the compound of formula I which is predominantly in the form of a complex with the Lewis acid.

It is believed that the reaction comprises two stages. In the first stage, one molecule of formula II reacts with one molecule of formula III to form the intermediate 4-(4-phenoxybenzoyl)benzoyl chloride of formula IV, which is called an "active intermediate":

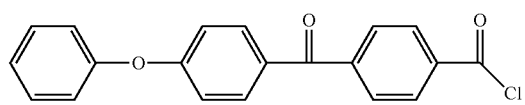
(IV)

Then one molecule of the active intermediate of formula IV reacts with another molecule of formula III to form the desired product of formula I.

During the reaction, 4-(4-phenoxybenzoyl)benzoic acid of formula IVa can also be produced to some extent (notably from the active intermediate of formula IV):

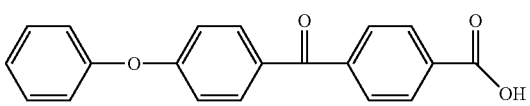
(IVa)

The corresponding 4-(4-phenoxybenzoyl)benzoic acid ester can be formed either directly from the acyl chloride of formula IV or from the carboxylic acid of formula IVa. The acid form and/or the ester form of the intermediate can be formed during the reaction but they can also primarily be formed from the remaining active intermediate during subsequent workup (such as when the product mixture is mixed with a protic solvent, as described below).

The 4-(4-phenoxybenzoyl)benzoic acid and 4-(4-phenoxybenzoyl)benzoic acid ester are inactive and therefore remain as impurities in the product mixture.

The other main impurities produced by the reaction are xanthydrol moiety-containing molecules.

The reaction solvent is preferably a non-protic solvent.

A protic solvent is a solvent containing at least one hydrogen atom bound to an oxygen or nitrogen atom, and which is therefore able to donate protons to reagents.

A non-protic solvent is a solvent which is not a protic solvent.

The non-protic solvent used herein can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene and mixtures thereof.

Ortho-dichlorobenzene is a preferred solvent.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is preferred.

The reaction between the compounds of formulas (II) and (III) to make the compound of formula (I) may be performed in a reactor. The reactor can be for instance a glass reactor, a glass-lined reactor or a stainless-steel reactor.

According to some variations, the materials introduced into the reactor in the method of embodiments of the invention consist essentially, or consist, of the compounds of formulas (II) and (III), the reaction solvent and the Lewis acid.

According to embodiments of the invention, an initial reactant mixture comprising (and preferably consisting of) terephthaloyl chloride and diphenyl ether in the reaction solvent is provided. The reactant mixture can be made by mixing the three components together, in any order. By way of example, the solvent can be introduced first in the reactor, and then the two reactants can be added to the reactor.

As a second step, the Lewis acid is added to the reactant mixture. Preferably, the Lewis acid is added as a solid. Alternatively, it can also be added as a suspension or a solution, preferably in the abovementioned solvent.

In some variations, the Lewis acid is added in a particulate form, such as in the form of granules (having, e.g., a Dv80 of more than 1 mm) or in the form of a powder (having, e.g., a Dv80 of less than 1 mm, and preferably a Dv50 of less than 0.5 mm). Dv80 and Dv50 are respectively the particle sizes at the $80^{th}$ and $50^{th}$ percentiles (in volume) of the cumulative size distribution of the Lewis acid particles. These parameters may be determined by sieving.

In some particular embodiments, the weight concentrations and weight ratios of the reactants and of the catalyst are as follows:
- the concentration of terephthaloyl chloride (relative to the sum of solvent, terephthaloyl chloride, diphenyl ether and Lewis acid introduced into the reactor) is from 3 to 12%, preferably from 5 to 10%;
- the concentration of diphenyl ether (relative to the sum of solvent, terephthaloyl chloride, diphenyl ether and Lewis acid introduced into the reactor) is from 5 to 35%, preferably from 12 to 25%;
- the concentration of Lewis acid (relative to the sum of solvent, terephthaloyl chloride, diphenyl ether and Lewis acid introduced into the reactor) is from 4 to 30%, preferably from 10 to 25%;
- the weight ratio of terephthaloyl chloride to diphenyl ether introduced into the reactor is from 0.2 to 0.6, preferably from 0.3 to 0.5;
- the weight ratio of Lewis acid to terephthaloyl chloride plus diphenyl ether introduced into the reactor is from 0.2 to 0.9, preferably from 0.3 to 0.7.

The addition of the Lewis acid is preferably performed progressively, over a period of time which can advantageously range from 5 to 600 minutes, preferably from 30 to 300 minutes.

The addition can be performed continuously or with one or more interruptions. If it is performed continuously, it can be conducted at a constant rate of addition. Alternatively, the rate of addition can vary over time.

The reactant mixture may be agitated during at least part of the reaction step. Thus, the reactor is preferably provided with an agitation device such as a mechanical stirrer (which may, e.g., comprise one or more impellers) or a recirculation loop with a pump.

Preferably, the reactant mixture may be agitated using the agitation device during the addition of the Lewis acid.

Once the addition of the Lewis acid to the reactant mixture is complete, the reaction step may optionally comprise a step of maintaining the reactant mixture, preferably under agitation, for a certain time, in order to complete the reaction to the desired degree. Preferably, the mixture is maintained from 0 to 600 min, more preferably from 5 to 180 min.

Once the reaction has been completed to the desired degree, the reactant mixture becomes designated as a product mixture.

The reaction at stake is exothermic. Preferably, a temperature control system is provided, in order to control the temperature of the reactant mixture in the reactor, in particular during and after addition of the Lewis acid. The temperature control system may in particular comprise a temperature sensor within the reactor and may be configured to cool and/or to heat the reactant mixture. Preferably, it is at least configured to cool the reactant mixture.

Devices for heating and/or cooling the reactant mixture may include a heat exchanger inside the reactor or in a recirculation loop, or a heat exchange fluid circuit in the jacket of the reactor.

When the temperature of the reactant mixture increases during the step of adding the Lewis acid, this can be achieved in three different manners:
- by heating the reactant mixture (while preferably also controlling the rate of addition of the Lewis acid, so as to achieve a targeted increase in temperature);
- by simply controlling the rate of addition of the Lewis acid so as to achieve a targeted increase in temperature, without providing external cooling or heating; or
- by cooling the reactant mixture, while also controlling the rate of addition of the Lewis acid, so as to achieve a targeted increase in temperature According to a preferred embodiment, the reactant mixture is cooled during and possibly also after the step of adding the Lewis acid, in order to prevent an excessively large or rapid increase in temperature of the reactant mixture as the reactants start reacting with each other.

Preferably, the temperature of the reactant mixture is greater than 5° C. during at least part of the step of adding the Lewis acid to the reactant mixture. In particular variations, the temperature of the reactant mixture is at least 10° C., or at least 15° C., or at least 20° C., or at least 25° C., or at least 30° C., or at least 35° C., or at least 40° C., or at least 45° C., or at least 50° C., or at least 55° C., or at least 60° C., during at least part of the step of adding the Lewis acid to the reactant mixture.

Conducting the reaction step at a relatively high temperature may result in an increase in the yield of 1,4-bis(4-phenoxybenzoylbenzene), without any significant increase in the level of by-product impurities such as xanthydrol moiety-containing molecules.

On the other hand, the temperature during the step of adding the Lewis acid to the reactant mixture should preferably remain below a certain threshold in order to avoid any significant polymerization of the reactants into a PEKK polymer.

Furthermore, the temperature during the step of adding the Lewis acid to the reactant mixture should remain below the boiling temperature of the solvent.

It is possible to operate the reactor in a pressurized manner so that the temperature in the reactor can reach a higher value without causing the solvent to boil. In this case, the pressure in the reactor can range from 1 bar (atmospheric pressure) to 6 bar, preferably from 1.5 bar to 3 bar.

Alternatively, and preferably, the reaction may be performed at atmospheric pressure.

According to some variants, the temperature of the reactant mixture does not exceed 100° C., preferably 90° C., more preferably 80° C., even more preferably 70° C., during the step of adding the Lewis acid.

The temperature of the reactant mixture can remain constant during the step of adding the Lewis acid. Alternatively, it can vary during this step.

In preferred variations, the temperature of the reactant mixture increases during the step of adding the Lewis acid, i.e., the final temperature is greater than the initial temperature.

In some embodiments, the temperature difference ΔT between the final temperature and the initial temperature is from 1 to 70° C., preferably from 5 to 60° C., more preferably from 10 to 50° C., and in particular from 20 to 40° C.

In some variations, the temperature of the reactant mixture continuously increases from the initial temperature to the final temperature. Alternatively, the temperature of the reactant mixture may comprise one or more increase stages and one more plateau stages during the step of adding the Lewis acid. In particular, the temperature of the reactant mixture may initially increase during a first part of the step of adding the Lewis acid, from the initial temperature to the final temperature, and then plateau at the final temperature during a second part of the step of adding the Lewis acid. In this case, the plateaued temperature may be set with a precision of, e.g., +/−5° C., or +/−2° C., or +/−1° C.

There is no limitation as to the temperature of the reactant mixture during the optional step of maintaining the reactant mixture, after the addition of the Lewis acid. In some variations, the temperature of the mixture is maintained at the final temperature described above. In other variations, it increases or decreases relative to the final temperature.

A method of embodiments of the invention may comprise steps (after the reaction has been completed to the desired degree) for purifying 1,4-bis(4-phenoxybenzoylbenzene) from the product mixture, and in particular from the solvent, catalyst and unreacted reactants as well as by-products.

In particular, said purification comprises the step of contacting the product mixture with a protic solvent, so as to recover a first phase containing the Lewis acid and a second phase containing 1,4-bis(4-phenoxybenzoylbenzene). The relative weight ratio of product mixture and protic solvent put in contact is preferably from 4 to 0.25, most preferably from 3 to 0.5, more preferably from 2 to 1.

The protic solvent can in particular be an organic solvent, such as methanol, acetic acid, formic acid, ethanol, isopropanol, and benzyl alcohol. Methanol is preferred as an organic solvent.

Alternatively, the protic solvent can be an aqueous solution.

Mixtures of the above solvents can also be used, such as an aqueous-organic solvent, e.g., an aqueous solution mixed with methanol.

Using an aqueous solution as the protic solvent for performing the dissociation of the 1,4-bis(4-phenoxybenzoylbenzene)-Lewis acid complex is especially advantageous for two reasons.

First, an aqueous solution has a relatively large heat capacity. This makes it possible to achieve a better dissipation of the heat generated as a result of the highly exothermic dissociation of the 1,4-bis(4-phenoxybenzoylbenzene)-Lewis acid complex. Less vapor may thus be generated than if, e.g., methanol is used. More generally, the safety of the process is improved.

Second, the Lewis acid is recovered in the aqueous solution. This aqueous stream can be more easily directly recycled and reused than, e.g., a methanol stream. For instance, when the Lewis acid is aluminum trichloride, the aqueous effluent of aluminum trichloride can be directly used as a flocculation agent in wastewater treatment. Conversely, aluminum trichloride in methanol is a waste effluent which should be disposed of.

The aqueous solution can be simply water. Alternatively, it can be an acidic solution, such as a solution of hydrochloric acid, phosphoric acid, sulfuric acid, nitric acid, an organic acid such as formic acid and any combination of these. Preferably, the pH of the aqueous solution is not more than 7, preferably not more than 6, or not more than 5, or not more than 4, or not more than 3, or not more than 2.

The dissociation of the 1,4-bis(4-phenoxybenzoylbenzene)-Lewis acid complex may be more efficient when an acidic solution is used.

A first possibility for contacting the 1,4-bis(4-phenoxybenzoylbenzene)-Lewis acid complex with the protic solvent is to add the protic solvent to the product mixture, for example directly in the reactor. The addition is preferably performed progressively, over a period of time which can advantageously range from 2 to 600 minutes, preferably from 10 to 180 minutes, more preferably from 20 to 60 minutes.

A second (preferred) possibility is to provide the protic solvent in a separate vessel and to subsequently add the product mixture to the protic solvent. The addition is preferably performed progressively, over a period of time which can advantageously range 2 to 600 minutes, preferably from 10 to 180 minutes, more preferably from 20 to 60 minutes.

Both in the first and second possibility, the mixture of protic solvent and product mixture may be preferably agitated, using, e.g., an agitation device such a mechanical stirrer (which may, e.g., comprise one or more impellers) or a recirculation loop with a pump.

A third possibility is to simultaneously feed the aqueous solution and the product mixture into a reactor or a pipe.

Once the entirety of the product mixture and of the aqueous solution have been put in contact, the mixture of both can be maintained, preferably with agitation, for a period of time of, e.g., from 1 to 600 minutes, preferably from 10 to 300 minutes, more preferably from 30 to 180 minutes.

Temperature may optionally be controlled at this stage, and for instance the mixture may be cooled. Temperature control and cooling devices as already mentioned above may be used to this end.

In an alternative variation, the temperature is not controlled at this stage, and it thus rises, possibly up to the boiling point of one or more of the solvents (including, e.g., water) present in the mixture. The steam thus generated can be collected and then treated and/or recycled or disposed of. The mixture can optionally cool down (or be actively cooled down) after this exothermic surge.

At the end of the step of contacting the product mixture with an aqueous solution, a first phase (containing protic solvent) and a second phase (containing reaction solvent) are obtained. If an aqueous solution is used as the protic solvent, the first phase is an aqueous phase and the second phase is an organic phase. 1,4-bis(4-phenoxybenzoylbenzene) is mostly present in the second phase, e.g., at least 50 wt % of the 1,4-bis(4-phenoxybenzoylbenzene) is present in the second phase, preferably more than 50 wt %, preferably at least 70 wt %, preferably at least 90 wt %, while the Lewis acid is mostly present in the first phase, e.g., at least 50 wt % of the Lewis acid is present in the first phase, preferably more than 50 wt %, preferably at least 70 wt %, preferably at least 90 wt %.

The first phase and second phase may be separated so as to be recovered separately, preferably by decantation. Accordingly, an upper phase may be transferred out from the top of the decantation device and/or a lower phase may be transferred from the bottom of the decantation device, to a second equipment. These transfers may be driven by one or more pumps, by gravity or by a difference in pressure.

The first phase contains the Lewis acid and can be further treated, or recycled, or disposed of, or preferably marketed or re-used in a different industrial process.

The second phase may contain 1,4-bis(4-phenoxybenzoylbenzene) mostly in a solid/precipitated form.

In some variations, the organic phase is optionally contacted again with a protic solvent, as described above, so as to recover again a first phase and a second phase. This operation may be repeated several times if desired, before the second phase is further treated.

In order to recover 1,4-bis(4-phenoxybenzoylbenzene) from the second phase, a solid/liquid separation step is performed by centrifugal filtration, in a centrifugal filtration device.

Alternatively, 1,4-bis(4-phenoxybenzoylbenzene) may be directly recovered from the mixture of first phase and second phase without prior separation of the first phase and second phase, by subjecting this mixture to a centrifugal filtration, in a centrifugal filtration device. In this case 1,4-bis(4-phenoxybenzoylbenzene) is retained on the filter, and the first phase and second phase are collected at an outlet of the centrifugal filtration device and may be separated at this time.

The centrifugal filtration device may in particular have a horizontal axis or a vertical axis.

Centrifugal filtration is preferably performed at an acceleration rate of from 2 to 1500 g, more preferably of from 5 to 1000 g, and most preferably of from 10 to 800 g.

Different acceleration values or ranges may be used during successive phases of centrifugal filtration, such as a loading phase, a washing phase and/or a dewatering phase. By way of example, a low acceleration may be applied first, followed by higher acceleration.

The dry solid matter content of the filtered product at the end of the filtration is preferably from 65 wt. % to 99 wt. %, more preferably from 70 wt. % to 98 wt. %, even more preferably from 80 to 97 wt. %, and most preferably from 90 to 96 wt. %.

In preferred variations, the efficiency of the solid/liquid separation step is improved by a so-called ripening step, which is performed before said solid/liquid separation step.

Indeed, it has now been found that the morphology of the solid form of 1,4-bis(4-phenoxybenzoylbenzene) is a parameter affecting the efficiency of the solid/liquid separation step. 1,4-bis(4-phenoxybenzoylbenzene) tends to be present after dissociation of the complex in the form of fine plate-like particles which are inconvenient to separate from the surrounding liquid. By performing a ripening step before the solid/liquid separation step, 1,4-bis(4-phenoxybenzoylbenzene) is partly dissolved and then recrystallized. This makes it possible to obtain a solid form of 1,4-bis(4-phenoxybenzoylbenzene) which is easier to separate from the surrounding liquid, in particular by centrifugal filtration. In particular, filterability of 1,4-bis(4-phenoxybenzoylbenzene) is improved owing to the ripening step.

In some variations, the ripening step is performed before the first phase and second phase are separated (so that both phases are subjected to the ripening step).

In other, preferred, variations, the ripening step is performed only on the second phase, after the first phase and second phase are separated.

In the ripening step, the second phase (pre-separated or not) is first heated up to a maximum temperature, and cooled down to a separation temperature. Therefore, 1,4-bis(4-phenoxybenzoylbenzene) gets partly dissolved in the second phase and recrystallizes as particles typically shaped as stacks of thin plates, which results in a more favorable morphology of the solid form of 1,4-bis(4-phenoxybenzoylbenzene) for the solid/liquid separation step.

It is preferred that 1,4-bis(4-phenoxybenzoylbenzene) does not get fully dissolved during the ripening step. Indeed, the presence of remaining solid 1,4-bis(4-phenoxybenzoylbenzene) particles in the second phase may make it possible to recrystallize 1,4-bis(4-phenoxybenzoylbenzene) in a relatively quick and efficient manner, since said remaining particles tend to act as crystallization seeds.

The maximum proportion of 1,4-bis(4-phenoxybenzoylbenzene) dissolved in the second phase during the ripening step (relative to the total amount of 1,4-bis(4-phenoxybenzoylbenzene)) can for instance be from 20 to 30 wt. %, or from 30 to 40 wt. %, or from 40 to 50 wt. %, or from 50 to 60 wt. %, or from 60 to 70 wt. %, or from 70 to 80 wt. %, or from 80 to 90 wt. %, or from 90 to 95 wt. %, or from 95 to 99 wt. %.

Typical devices for heating the second phase and controlling the temperature are as described above.

The maximum temperature reached during the ripening step may be for instance from 80 to 90° C., or from 90 to 100° C., or from 100 to 110° C., or from 110 to 120° C., or from 120 to 130° C., or from 130 to 140° C., or from 140 to 150° C., or from 150 to 160° C. The selection of the maximum temperature depends on the nature of the non-protic solvent and of the protic solvent used in the method. A temperature range of from 110 to 135° C. has been found particularly advantageous when ortho-dichlorobenzene is used as a non-protic solvent and an aqueous solution is used as a protic solvent.

Depending on the desired maximum temperature, it may be necessary to separate the first phase from the second phase before the ripening step. For instance, water forms an azeotrope with ortho-dichlorobenzene, having a low boiling point at atmospheric pressure of 98° C. Therefore, it is preferred to separate the first phase from the second phase before the ripening step, if the protic solvent is an aqueous solvent and if the non-protic solvent is ortho-dichlorobenzene, so that a desired maximum temperature for the second phase of, e.g., from 110 to 135° C. can be effectively reached, at atmospheric pressure.

According to other variations, part or all of the ripening step is performed under pressure, for instance at an absolute pressure of from 1.5 to 2 bar, or from 2 to 5 bar, or from 5 to 10 bar, or from 10 to 20 bar, or from 20 to 50 bar. This may in particular make it possible to reach the desired maximum temperature for the second phase without previously separating it from the first phase.

The heating rate during the ripening step may be for instance from 0.1 to 10° C./min, preferably from 0.2 to 5° C./min, more preferably from 0.5 to 1° C./min.

Once the maximum temperature has been reached, the second phase (pre-separated or not) can optionally be maintained at the maximum temperature, preferably for 1 to 600 min, more preferably from 5 to 300 min, more preferably from 15 to 120 min.

Then, the second phase (pre-separated or not) is cooled down in a controlled manner, using cooling and temperature control systems as already described above. The cooling rate is preferably sufficiently low so that 1,4-bis(4-phenoxybenzoylbenzene) properly crystallizes, but not excessively low so as to optimize the overall economic efficiency of the embodiments of method of the invention. The cooling rate may for instance be from 5 to 10° C./h, or from 10 to 15° C./h, or from 15 to 20° C./h, or from 20 to 25° C./h, or from 25 to 30° C./h, or from 30 to 35° C./h, or from 35 to 40° C./h, or from 40 to 45° C./h, or from 45 to 50° C./h, or from 50 to 55° C./h, or from 55 to 60° C./h. Rates comprised between 20 and 40° C./h and notably between 25 and 35° C./h have been found to be particularly advantageous.

In some (preferred) variations, the temperature may decrease at a substantially constant rate during this cooling down stage. In other variations, the temperature may decrease at a non-constant rate. In such cases, the rate ranges mentioned above are meant to be average rates over the entire cooling down stage.

At the end of the ripening stage, the second phase (pre-separated or not) reaches the so-called separation temperature, which is less than the maximum temperature.

The proportion of solid 1,4-bis(4-phenoxybenzoylbenzene) in the second phase (relative to the total amount of 1,4-bis(4-phenoxybenzoylbenzene)) at the end of the ripening step, i.e., at the separation temperature, is preferably at least 90 wt. %, and more preferably at least 95 wt. %, or at least 98 wt. %, or at least 99 wt. %, or at least 99.5 wt. %, or at least 99.9 wt. %.

A characteristic of a suspension commonly used to describe its ability to be filtered is the cake specific resistance. The cake specific resistance of 1,4-bis(4-phenoxybenzoylbenzene) after the ripening step is preferably at least twice as low, more preferably three times as low, or five times as low, or ten times as low as the cake specific resistance of 1,4-bis(4-phenoxybenzoylbenzene) before the ripening step. The cake specific resistance $R_s$ can be calculated by plotting the filtration time divided by the filtered volume (t/V) as a function of the filtered volume (V), by measuring the slope of the corresponding graph in the area where the regime is substantially linear, and by referring to the following Kozeny-Carman equation: $t=(R_0 \cdot \mu \cdot V)/(A \cdot \Delta P)+(R_s \cdot \mu \cdot W \cdot V^2)/(2\ A^2 \cdot \Delta P)$, wherein t is the filtration time expressed in s, $R_0$ is the specific resistance of the filtering medium expressed in $m^{-1}$, $\mu$ is the viscosity of the filtrate at the filtration temperature in Pa·s, V is the filtered volume at time t expressed in $m^3$, A is the filtration surface is $m^2$, $\Delta P$ is the pressure drop across the filter (including the cake and the filtering medium) expressed in Pa, W is the dry solid concentration of the suspension to be filtered in $kg/m^3$ and $R_s$ is the cake specific resistance in m/kg. Additional details for how to conduct the measurement method may be found in the examples below.

The cake specific resistance of 1,4-bis(4-phenoxybenzoylbenzene) after the ripening step is preferably from $5 \times 10^7$ m/kg to $1.5 \times 10^{10}$ m/kg, more preferably from $1 \times 10^8$ m/kg to $1 \times 10^{10}$ m/kg, more preferably from $2 \times 10^8$ m/kg to $5 \times 10^9$ m/kg.

The solid/liquid separation step (preferably a filtration step) is preferably performed at the separation temperature defined above.

In case no ripening step is present, the second phase can be either directly obtained at this separation temperature after separating it from the first phase, or directly heated up or cooled down to the separation temperature after separating it from the first phase, or directly brought to the separation temperature and subjected to the solid/liquid separation step without being separated from the first phase beforehand.

The separation temperature can, e.g., generally range from −20 to 0° C., or from 0 to 20° C., or it can be at least 20° C., such as 20° C. to 120° C. A separation temperature of at least 20° C. is preferred, especially (but not exclusively) if an aqueous solution is used as a protic solvent, for the following reasons.

In order to achieve a high purity of the final 1,4-bis(4-phenoxybenzoylbenzene), it is desirable to eliminate or reduce the amount of, in particular, the 4-(4-phenoxybenzoyl)benzoic acid and 4-(4-phenoxybenzoyl)benzoic acid ester impurities.

Without wishing to be bound by any theory, the present inventors have come to appreciate that 4-(4-phenoxybenzoyl)benzoic acid is less soluble than 4-(4-phenoxybenzoyl)benzoic acid esters in the reaction solvent; and that contacting the product mixture with an aqueous solution results in a greater proportion of 4-(4-phenoxybenzoyl)benzoic acid (relative to the total of 4-(4-phenoxybenzoyl)benzoic acid and 4-(4-phenoxybenzoyl)benzoic acid ester) than contacting the product mixture with a non-aqueous solvent such as methanol.

It is desirable for all 4-(4-phenoxybenzoyl)benzoic acid-type impurities to be as solubilized as possible in the second phase. Indeed, solid particles of 4-(4-phenoxybenzoyl)benzoic acid-type impurities tend to be retained with the solid 1,4-bis(4-phenoxybenzoylbenzene) during the solid/liquid separation step.

As a result, the use of an aqueous solution for the dissociation of the 1,4-bis(4-phenoxybenzoylbenzene)-Lewis acid complex, which is advantageous for the reasons mentioned above, may pose a problem for the separation of 4-(4-phenoxybenzoyl)benzoic acid-type impurities.

Therefore, in preferred variations, in order to solve this problem and make sure that the separation of 4-(4-phenoxybenzoyl)benzoic acid-type impurities is optimal, the solid/liquid separation step is performed at a temperature of at least 20° C. Possible temperature ranges for this step are in particular from 20 to 25° C., from 25 to 30° C., from 30 to 35° C., from 35 to 40° C., and from 40 to 45° C.

If the temperature is relatively high, 4-(4-phenoxybenzoyl)benzoic acid is better solubilized in the second phase. On the other hand, the temperature should not be excessively high, otherwise 1,4-bis(4-phenoxybenzoylbenzene) itself may also get substantially solubilized and therefore lost during the solid/liquid separation step.

In order to maintain the desired temperature during the liquid/solid separation step, use may be made of a temperature control system and cooling and/or heating devices as described above.

Solid 1,4-bis(4-phenoxybenzoylbenzene), together with residual impurities, is recovered after the solid/liquid separation step.

In preferred variations, said solid 1,4-bis(4-phenoxybenzoylbenzene) is further purified by washing it in a protic solvent. The use of a protic solvent is advantageous as 1,4-bis(4-phenoxybenzoylbenzene) is highly insoluble in such a solvent. The protic solvent at this stage can be an aqueous solution. However, in preferred variations, the protic solvent at this stage is an organic solvent. Methanol is a particularly preferred solvent. Other possibilities include, e.g., acetic acid, formic acid, ethanol, isopropanol, and benzyl alcohol.

The use of an organic solvent such as methanol during this washing step is advantageous since 4-(4-phenoxybenzoyl) benzoic acid-type impurities, and in particular 4-(4-phenoxybenzoyl)benzoic acid itself, are more soluble in such a solvent than in water, while on the other hand 1,4-bis(4-phenoxybenzoylbenzene) is still poorly soluble.

The weight ratio of solid 1,4-bis(4-phenoxybenzoylbenzene) to protic solvent used at this washing step may be, e.g., be from 0.3 to 20, preferably from 0.6 to 10, more preferably from 1 to 5.

After the washing step or concomitantly with the washing step, another solid/liquid separation step may be performed.

The washing step may be performed by mixing the solid 1,4-bis(4-phenoxybenzoylbenzene) recovered at the previous step with the protic solvent in a vessel. The duration of such a washing step may be, e.g., from 5 to 900 min, preferably from 15 to 300 min, more preferably from 45 to 120 min.

However, in preferred variations, use is made of a centrifugal filtration device, so that washing and filtering may be performed concomitantly in this device, without resuspending the product.

The washing step and the subsequent or concomitant solid/liquid separation step are preferably performed at a temperature of at least 20° C. Operating at relatively high temperature is advantageous for the reasons already mentioned above, i.e., this helps solubilize 4-(4-phenoxybenzoyl)benzoic acid-type impurities, and in particular 4-(4-phenoxybenzoyl)benzoic acid itself.

It may be advantageous to operate at a higher temperature during the washing step and subsequent or concomitant solid/liquid separation step than during the initial solid/liquid separation step, as 1,4-bis(4-phenoxybenzoylbenzene) is very insoluble in protic solvents. It may thus be possible to operate at a temperature up to the boiling point of the protic solvent which is used.

Possible temperature ranges for these steps are in particular from 20 to 25° C., from 25 to 30° C., from 30 to 35° C., from 35 to 40° C., from 40 to 45° C., from 45 to 50° C., from 50 to 55° C., and from 55 to 60° C.

Temperature control during these steps can be performed as described above.

The washing and solid/liquid separation (preferably centrifugal centrifugation) steps may optionally be repeated one or more times, in exactly the same manner or in a different manner. For example, different protic solvents, different washing durations and/or different temperatures may be used in the various washing and solid/liquid separation steps.

At each centrifugal filtration, an acceleration rate of preferably from 2 to 1500 g, more preferably of from 5 to 1000 g, and most preferably of from 10 to 800 g, may be used.

At each centrifugal filtration, the dry solid matter content of the filtered product at the end of the filtration may be from 85 wt. % to 99 wt. %, more preferably from 88 wt. % to 98 wt. % and most preferably from 90 to 97 wt. %.

After the last solid/liquid separation, the recovered solid may be dried, preferably at atmospheric pressure or under vacuum in an oven or a dryer.

Ultimately, 1,4-bis(4-phenoxybenzoylbenzene) in a substantially pure form, i.e., at a purity of at least 98.5 wt. %, preferably 99.0 wt. % and more preferably 99.5 wt. %, is recovered.

The purity of 1,4-bis(4-phenoxybenzoylbenzene) may be determined by a number of methods, including nuclear magnetic resonance, differential scanning calorimetry, gas chromatography or high-performance liquid chromatography (HPLC). Preferably, said purity is determined by HPLC.

The 1,4-bis(4-phenoxybenzoylbenzene) obtained according to embodiments of the invention can subsequently be used to perform a polymerization reaction so as to make a PEKK polymer.

In order to make the PEKK polymer, 1,4-bis(4-phenoxybenzoylbenzene) is reacted with at least one difunctional aromatic acyl chloride.

The difunctional aromatic acyl chloride may in particular include terephthaloyl chloride, isophthaloyl chloride and more preferably a mixture of terephthaloyl chloride and isophthaloyl chloride.

The reaction is preferably implemented in a solvent. The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene and mixtures thereof. Ortho-dichlorobenzene is a preferred solvent.

The reaction is preferably implemented in the presence of a Lewis acid as a catalyst.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is preferred.

The polymerization can be implemented in the same reactor as the one used for the production of 1,4-bis(4-phenoxybenzoylbenzene). But more preferably it is implemented in one or more other reactors.

The polymerization can be carried out at a temperature ranging from, e.g., 50 to 120° C.

The method of making the PEKK polymer advantageously also comprises one or more steps for purifying the PEKK polymer, such as steps of:
  mixing the mixture containing the PEKK polymer with a
    protic solvent so as to provide a PEKK slurry;

separating the PEKK polymer from the PEKK slurry, preferably by filtration and washing.

The protic solvent used to make the PEKK slurry may be, e.g., methanol.

The PEKK polymer can then be recovered from the PEKK slurry by filtration. If necessary, the polymer can be washed, preferably by a protic solvent such as methanol, and filtrated again, once or several times. Washing can be performed for example by re-slurrying the polymer in the solvent.

EXAMPLES

The following examples illustrate embodiments of the invention without limiting the invention.

Example 1

In a 2 L reactor equipped with a mechanical stirrer, with a nitrogen inlet and an outlet going to a scrubber system, 1066 g of ortho-dichlorobenzene, 92.7 g of terephthaloyl chloride and 233 g of diphenyl ether were introduced. After full solubilization, the mixture was set at 35° C. While keeping the temperature at 35° C., 198 g of aluminum trichloride was slowly added over 3 h to the reactant mixture. After completion of aluminum trichloride addition, the mixture was kept agitated at 35° C. during 3 h to finish the reaction. The mixture was then poured into a second reactor containing 830 g of water containing 3% HCl. After completion of this step, the mixture was settled during 3 h so that the aqueous phase could decant and be removed by suction. A second 3% HCl aqueous phase was then added, stirred and then settled during 1 h for decantation. This second acidic aqueous phase was also removed by suction.

The suspension thus obtained was then heated up to 120° C., and cooled down to 35° C. in 3 h. The solid obtained was then separated from the solvent in a centrifuge at an acceleration of 760 g (1 g=9.80665 m·s$^{-2}$). After removal of the mother liquor, the wet powder was kept in the centrifuge and spray-washed with 1900 g of methanol at 35° C. A wet solid was thus obtained and removed from the centrifuge, having a solids content of 96 wt. % as measured by its weight loss on drying. It was then dried overnight under vacuum. 183 g of 1,4-bis(4-phenoxybenzoylbenzene) were thus recovered, with a purity of about 99.75% as determined by HPLC.

Example 2 (Centrifuge)

8336 g of a suspension of 1,4-bis (4-phenoxybenzoylbenzene) in organic solvent as obtained after cooling to 35° C. in example 1 was introduced over 2 minutes into a centrifuge (Model RC30 manufactured by Rousselet-Robatel), followed by a 2 minutes step of "de-watering" the cake from its mother liquor. Then 7125 g of methanol was sprayed on the wet cake over about 12 minutes while the centrifuge was still on rotation. It was then followed by "de-watering" during 2 minutes at high acceleration.

The overall duration of this purification sequence was 18 minutes. The purity of the 1,4-bis (4-phenoxybenzoylbenzene) obtained as measured by NMR was 99.62%.

Comparative Example (Filtration)

180 g of a suspension of 1,4-bis (4-phenoxybenzoylbenzene) in organic solvent as obtained after cooling to 35° C. in example 1 was placed in a glass sintered filter (pore size between 16 and 40 microns), and filtered under vacuum (200 mbar absolute). After 5 minutes, the vacuum was set to off and 13 g of methanol was gently poured on top of the wet cake obtained, and then made to percolate through the wet cake over 2 minutes, under vacuum. The wet powder obtained was then removed from the filter, placed in a flask with 78 g of methanol and agitated during 1 hour. This mixture was then filtered with the same equipment in approximately 5 minutes. The operation was repeated with another 78 g of methanol.

The overall duration of this purification sequence was 137 minutes. The purity of the 1,4-bis (4-phenoxybenzoylbenzene) obtained as measured by NMR was 99.68%.

Example 3

A synthesis similar to Example 1 was carried out. After the removal of the second acidic aqueous phase, the remaining organic suspension was heated up to 118° C. and then cooled down at 23° C. in 3 h.

80 mL of the organic suspension of 1,4-bis(4-phenoxybenzoyl-benzene) was placed in a 100 mL stainless steel pressure filter holder (EMD Millipore©) fitted with a polypropylene filtration cloth (pore size=35 microns).

Below this filter, a flask was placed on a scale. The system was then closed tightly and nitrogen pressure (typically between 1.1 and 2 bars absolute) was applied to the upper part of the system 30 seconds after introduction of the suspension.

The amount of filtrate collected in the flask was registered as a function of time. After conversion of the mass data into Volume using the density of the liquid, the filtration time divided by the filtered volume (t/V) was plotted as a function of the filtered volume (V) (see FIG. 1).

The slope of the graph in the area where the regime is substantially linear was measured and inserted into the Kozeny-Carman equation mentioned above, along with the following values for this example: $\mu=1.38 \cdot 10^{-3}$ Pa·s; $A=0.000934819$ m$^2$; $\Delta P=10000$ Pa and $W=160$ kg/m$^3$.

The cake specific resistance Rs according to Kozeny-Carman is then equal to (slope·2 A$^2$·$\Delta P$)/($\mu$·W)=1.58·10$^{10}$ m/kg.

Embodiments

1. A method for manufacturing 1,4-bis(4-phenoxybenzoylbenzene), comprising:
    reacting terephthaloyl chloride with diphenyl ether in a reaction solvent and in the presence of a Lewis acid, so as to obtain a product mixture comprising a 1,4-bis(4-phenoxybenzoylbenzene)-Lewis acid complex;
    contacting the product mixture with a protic solvent, so as to obtain a first phase containing the Lewis acid and a second phase containing 1,4-bis(4-phenoxybenzoylbenzene);
    subjecting at least the second phase to a solid/liquid separation step by centrifugal filtration, so as to recover solid 1,4-bis(4-phenoxybenzoylbenzene).
2. The method of embodiment 1, comprising one or more steps of washing the recovered solid 1,4-bis(4-phenoxybenzoylbenzene) in a protic solvent, preferably methanol, and subjecting it to a further solid/liquid separation, preferably by centrifugal filtration.
3. The method of embodiment 2, wherein at least one of the steps of washing the solid 1,4-bis(4-phenoxybenzoylbenzene) is performed at a temperature of at least 20° C., preferably at a temperature of from 30 to 60° C.

4. The method of embodiment 2 or 3, wherein each step of washing the recovered the solid 1,4-bis(4-phenoxybenzoylbenzene) is performed in a centrifugal filtration device.

5. The method of any one of embodiments 1 to 4, further comprising:
separating the first phase from the second phase, preferably before subjecting the second phase to the solid/liquid separation step; and/or
heating the second phase up to a maximum temperature, followed by cooling the second phase down to a separation temperature, before subjecting the second phase to the solid/liquid separation step, and preferably after separating the first phase from the second phase.

6. The method of embodiment 5, wherein from 30 to 99.9 wt. %, preferably from 50 to 95 wt. %, more preferably from 60 to 90 wt. % of the 1,4-bis(4-phenoxybenzoylbenzene) contained in the second phase is dissolved in the second phase at the maximum temperature.

7. The method of embodiment 5 or 6, wherein the maximum temperature is from 90 to 150° C., preferably from 100 to 140° C., more preferably from 110 to 135° C.

8. The method of any one of embodiments 5 to 7, wherein the separation temperature is at least 20° C., preferably is from 25 to 40° C.

9. The method of any one of embodiments 5 to 8, wherein the second phase is cooled down at a rate of from 10 to 50° C./h, preferably from 20 to 40° C./h.

10. The method of any one of embodiments 1 to 9, wherein the protic solvent that the product mixture is contacted with is an aqueous solution, which preferably has a pH of not more than 5, more preferably not more than 3 and most preferably not more than 2.

11. The method of any one of embodiments 1 to 10, wherein the product mixture is poured into a vessel containing the protic solvent.

12. The method of any one of embodiments 1 to 11, wherein the second phase is subjected to the solid/liquid separation step at a temperature of at least 20° C., preferably from 25 to 40° C.

13. The method of any one of embodiments 1 to 12, wherein the Lewis acid is aluminum trichloride.

14. The method of any one of embodiments 1 to 13, wherein the reaction solvent is ortho-dichlorobenzene.

15. A method of making a polyether ketone ketone polymer, comprising:
manufacturing 1,4-bis(4-phenoxybenzoylbenzene) according to the method of any one of embodiments 1 to 14;
reacting said 1,4-bis(4-phenoxybenzoylbenzene) with at least one difunctional aromatic acyl chloride.

The invention claimed is:

1. A method for manufacturing 1,4-bis(4-phenoxybenzoylbenzene), comprising:
reacting terephthaloyl chloride with diphenyl ether in a reaction solvent and in the presence of a Lewis acid, so as to obtain a product mixture comprising a 1,4-bis(4-phenoxybenzoylbenzene)-Lewis acid complex;
contacting the product mixture with a protic solvent, so as to obtain a first phase containing the Lewis acid and a second phase containing 1,4-bis(4-phenoxybenzoylbenzene);
subjecting at least the second phase to a solid/liquid separation step by centrifugal filtration, so as to recover solid 1,4-bis(4-phenoxybenzoylbenzene).

2. The method of claim 1, comprising one or more steps of washing the recovered solid 1,4-bis(4-phenoxybenzoylbenzene) in a protic solvent and subjecting it to a further solid/liquid separation.

3. The method of claim 2, wherein at least one of the steps of washing the solid 1,4-bis(4-phenoxybenzoylbenzene) is performed at a temperature of at least 20° C.

4. The method of claim 2, wherein each step of washing the recovered the solid 1,4-bis(4-phenoxybenzoylbenzene) is performed in a centrifugal filtration device.

5. The method of claim 1, further comprising:
separating the first phase from the second phase; and/or
heating the second phase up to a maximum temperature, followed by cooling the second phase down to a separation temperature, before subjecting the second phase to the solid/liquid separation step.

6. The method of claim 5, wherein from 30 to 99.9 wt. % of the 1,4-bis(4-phenoxybenzoylbenzene) contained in the second phase is dissolved in the second phase at the maximum temperature.

7. The method of claim 5, wherein the maximum temperature is from 90 to 150° C.

8. The method of claim 5, wherein the separation temperature is at least 20° C.

9. The method of claim 5, wherein the second phase is cooled down at a rate of from 10 to 50° C./h.

10. The method of claim 1, wherein the protic solvent that the product mixture is contacted with is an aqueous solution.

11. The method of claim 1, wherein the product mixture is poured into a vessel containing the protic solvent.

12. The method of claim 1, wherein the second phase is subjected to the solid/liquid separation step at a temperature of at least 20° C.

13. The method of claim 1, wherein the Lewis acid is aluminum trichloride.

14. The method of claim 1, wherein the reaction solvent is ortho-dichlorobenzene.

15. A method of making a polyether ketone ketone polymer, comprising:
manufacturing 1,4-bis(4-phenoxybenzoylbenzene) according to the method of claim 1;
reacting said 1,4-bis(4-phenoxybenzoylbenzene) with at least one difunctional aromatic acyl chloride.

* * * * *